US010561364B2

(12) United States Patent
Giridharagopalan et al.

(10) Patent No.: US 10,561,364 B2
(45) Date of Patent: Feb. 18, 2020

(54) PHYSIOLOGICAL SENSOR SYSTEM

(71) Applicant: Archis Health Investments LLC, Eden Prairie, MN (US)

(72) Inventors: Subhalakshmi Giridharagopalan, Eden Prairie, MN (US); Jayant Parthasarathy, Eden Prairie, MN (US)

(73) Assignee: Archis Health Investments LLC, Eden Prairie, MN (US)

( * ) Notice: Subject to any disclaimer, the term of this patent is extended or adjusted under 35 U.S.C. 154(b) by 196 days.

(21) Appl. No.: 15/782,456

(22) Filed: Oct. 12, 2017

(65) Prior Publication Data

US 2018/0098734 A1 Apr. 12, 2018

Related U.S. Application Data

(60) Provisional application No. 62/407,067, filed on Oct. 12, 2016.

(51) Int. Cl.
*A61B 5/00* (2006.01)
*A61B 5/1455* (2006.01)
*A61B 5/0205* (2006.01)

(52) U.S. Cl.
CPC ............ *A61B 5/6829* (2013.01); *A61B 5/002* (2013.01); *A61B 5/0015* (2013.01); *A61B 5/0205* (2013.01); *A61B 5/14552* (2013.01); *A61B 5/6807* (2013.01); *A61B 5/6826* (2013.01); *A61B 2505/07* (2013.01); *A61B 2562/225* (2013.01)

(58) Field of Classification Search
CPC ............ A61B 5/6801–68335; A61B 5/14552
See application file for complete search history.

(56) References Cited

U.S. PATENT DOCUMENTS

| | | | |
|---|---|---|---|
| 6,470,199 B1 | 10/2002 | Kopotic | |
| 6,669,627 B1* | 12/2003 | Campbell | A61N 5/0618 600/27 |
| 2005/0190065 A1* | 9/2005 | Ronnholm | A61M 21/00 340/575 |
| 2006/0258921 A1* | 11/2006 | Addison | A61B 5/0002 600/323 |
| 2010/0210924 A1 | 8/2010 | Parthasarathy | |
| 2014/0378812 A1* | 12/2014 | Saroka | A61B 5/6843 600/407 |
| 2015/0303619 A1* | 10/2015 | Kockx | A61N 1/048 607/149 |

* cited by examiner

*Primary Examiner* — Devin B Henson
*Assistant Examiner* — Huong Q Nguyen
(74) *Attorney, Agent, or Firm* — Neustel Law Offices

(57) ABSTRACT

A physiological sensor system for removably securing a physiological sensor to a garment. The physiological sensor system generally includes a physiological sensor adapted to be removably connected to a garment. The sensor may be adapted to detect a physiological condition, such as oxygen level or pulse rate. The sensor may include a connector such as a magnetic ring or hook-and-loop fastener to removably connect the sensor to the garment. The garment may include a window through which a light beam from the sensor may pass to illuminate the underlying body and sense various conditions. A control unit may be provided for controlling the sensor and processing data received therefrom.

18 Claims, 12 Drawing Sheets

PHYSIOLOGICAL SENSOR SYSTEM

CROSS REFERENCE TO RELATED APPLICATIONS

I hereby claim benefit under Title 35, United States Code, Section 119(e) of U.S. provisional patent application Ser. No. 62/407,067 filed Oct. 12, 2016. The 62/407,067 application. The 62/407,067 application is hereby incorporated by reference into this application.

STATEMENT REGARDING FEDERALLY SPONSORED RESEARCH OR DEVELOPMENT

Not applicable to this application.

BACKGROUND

Field

Example embodiments in general relate to a sensor system for removably securing a physiological sensor to a garment.

Related Art

Any discussion of the related art throughout the specification should in no way be considered as an admission that such related art is widely known or forms part of common general knowledge in the field.

Physiological sensors have been in use for many years. Typical physiological sensors may include pulse oximeters which function by directing a light onto a portion of a body such as the forehead, fingertip, or toe. Analysis of the reflected light can be used to determine pulse and oxygenation levels. Such sensors are commonly used in hospitals, but can be required for home use as well (such as in patients with apnea that can affect oxygen levels during sleep).

In the past, such sensors have been attached directly to the body in a number of ways. A very common sensor configuration utilizes a clip that clips the sensor onto the finger or toe. Such a configuration can be very uncomfortable for the patient; particularly if worn for long periods of time which can result in pressure sores or other discomfort.

Other sensors may utilize suction cups that attach directly to the skin, such as to the forehead. These body-attached sensors can often become dislodged or otherwise moved which can affect their operation. For example, if a patient rolls around and the clip or elastic band becomes partially disconnected, reads can be impacted.

SUMMARY

An example embodiment is directed to a physiological sensor system. The physiological sensor system includes a physiological sensor adapted to be removably connected to a garment. The sensor may be adapted to detect a physiological condition, such as oxygen level or pulse rate. The sensor may include a connector such as a magnetic ring or hook-and-loop fastener to removably connect the sensor to the garment. The garment may include a window through which a light beam from the sensor may pass to illuminate the underlying body and sense various conditions. A control unit may be provided for controlling the sensor and processing data received therefrom.

There has thus been outlined, rather broadly, some of the embodiments of the physiological sensor system in order that the detailed description thereof may be better understood, and in order that the present contribution to the art may be better appreciated. There are additional embodiments of the physiological sensor system that will be described hereinafter and that will form the subject matter of the claims appended hereto. In this respect, before explaining at least one embodiment of the physiological sensor system in detail, it is to be understood that the physiological sensor system is not limited in its application to the details of construction or to the arrangements of the components set forth in the following description or illustrated in the drawings. The physiological sensor system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
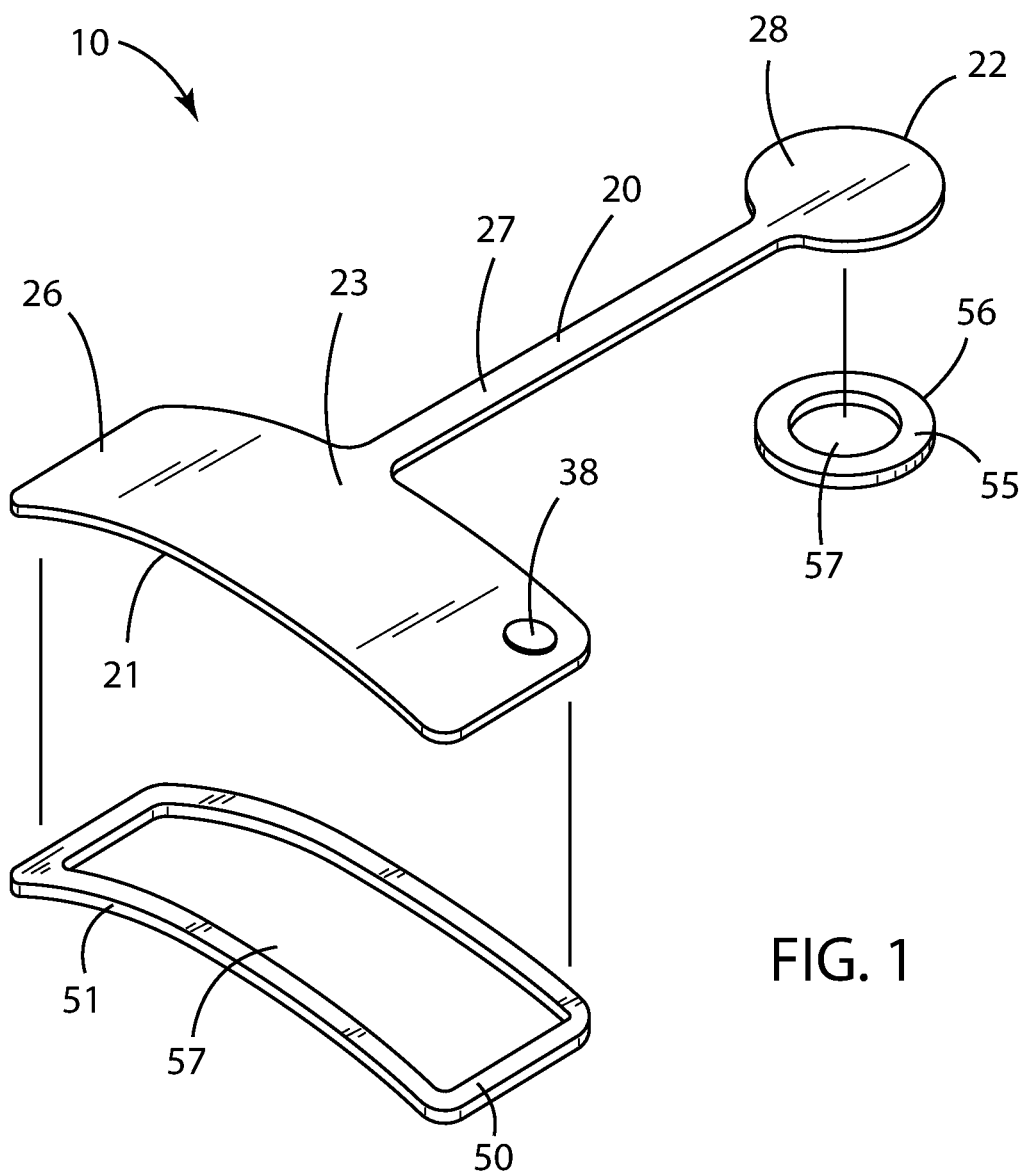
FIG. 1 is an upper perspective view of a physiological sensor system with connectors aligned for attachment in accordance with an example embodiment.

A. Overview.

An example physiological sensor system 10 generally comprises a garment 60 adapted to contact a portion of a body 12 of a wearer of the garment 60. A window 63 is formed in the garment 60; with the portion of the body 12 being visible through the window 63. A sensor 40 is connected to the garment 60 for detecting a physiological condition. The sensor 40 may be removably connected to the garment 60 above the window 63. A control unit 30 is provided for receiving and processing data from the sensor 40; with the control unit 30 being communicatively interconnected (via conduit 29 or wirelessly) with the sensor 40. An indicator 38 is provided which is communicatively interconnected with the control unit 30 and adapted to provide an indication of the physiological condition detected by the sensor 40. The indicator 38 may also in some embodiments provide an indication of the functional operating condition of the sensor 40 (such as indicating whether the sensor is active or not active).

The garment 60 may include a garment connector 62, 65 adapted to engage with the sensor 40 so as to removably connect the sensor 40 to the garment 60. In some embodiments, the garment connector 65 may comprise a first ring magnet which surrounds the window 66. The garment connector 65 may removably secure the control unit 30 to the garment 60 in some embodiments. In such embodiments, the sensor 40 may comprise a second ring magnet 55 adapted to removably engage with the garment connector 65 to removably connect the sensor 40 to the garment 60. In other embodiments, the sensor 40 may comprise a hook-and-loop fastener such as Velcro which is adapted to removably engage with the garment 60.

A control unit 30 may be communicatively interconnected with the sensor 40. The control unit 30 may be wirelessly connected to the sensor 40, or may be connected by a conduit 29 which is connected between the control unit 30 and the sensor 40. The control unit 30 may comprise a power source 32, a microcontroller 34, and a transceiver 36; with the transceiver 36 being communicatively interconnected with the sensor 40. The indicator 38 may comprise a light, a speaker, or a display. In some embodiments, the indicator 38 may comprise a mobile device such as a smart phone which is communicatively interconnected with the control unit 30.

The sensor 40 may include a reflectance probe; with the reflectance probe being adapted to direct light through the window and on to the portion of the body 12. In some embodiments, the sensor 40 may also receive light reflected from the body 12. A sleeve 25 may be secured around the sensor 40; with the sleeve 25 being removably connected to the garment 60. The window 63 may comprise an opening or may be covered by a material such as a semi-transparent material or a transparent material. The sensor 40 may be comprised of an optical sensor, such as a pulse oximeter reflectance probe adapted to detect an oxygen saturation level and a pulse rate. The sensor 40 may also be comprised of an accelerometer adapted to detect positional data of the person wearing the sensor 40.

B. Housing.

Figure 2:
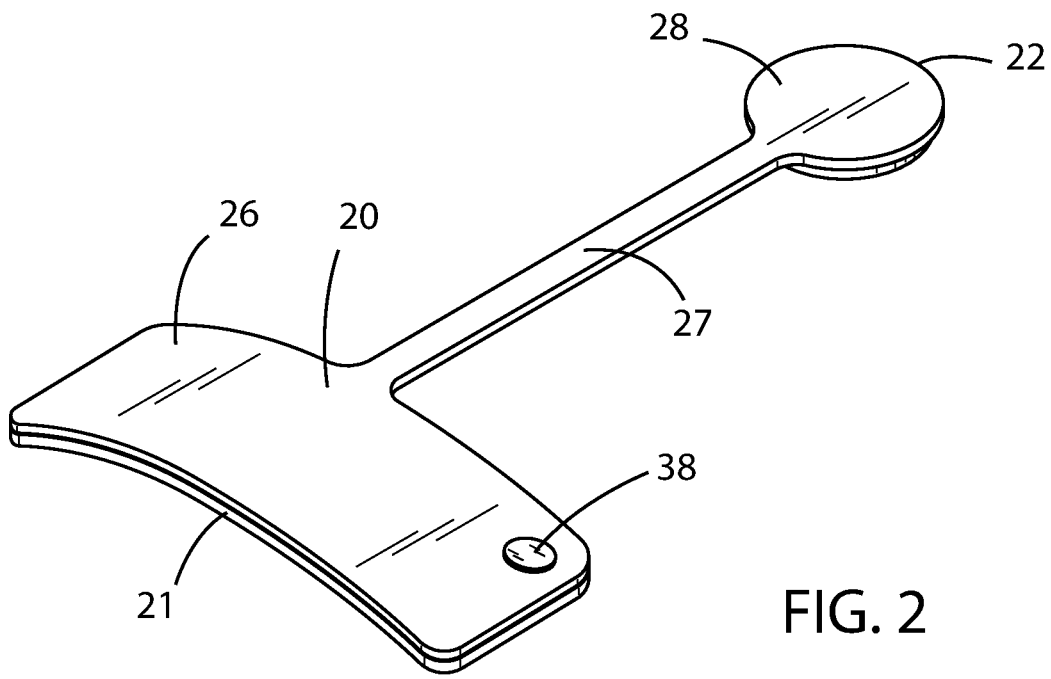
FIG. 2 is an upper perspective view of a physiological sensor system in accordance with an example embodiment.
Figure 3:
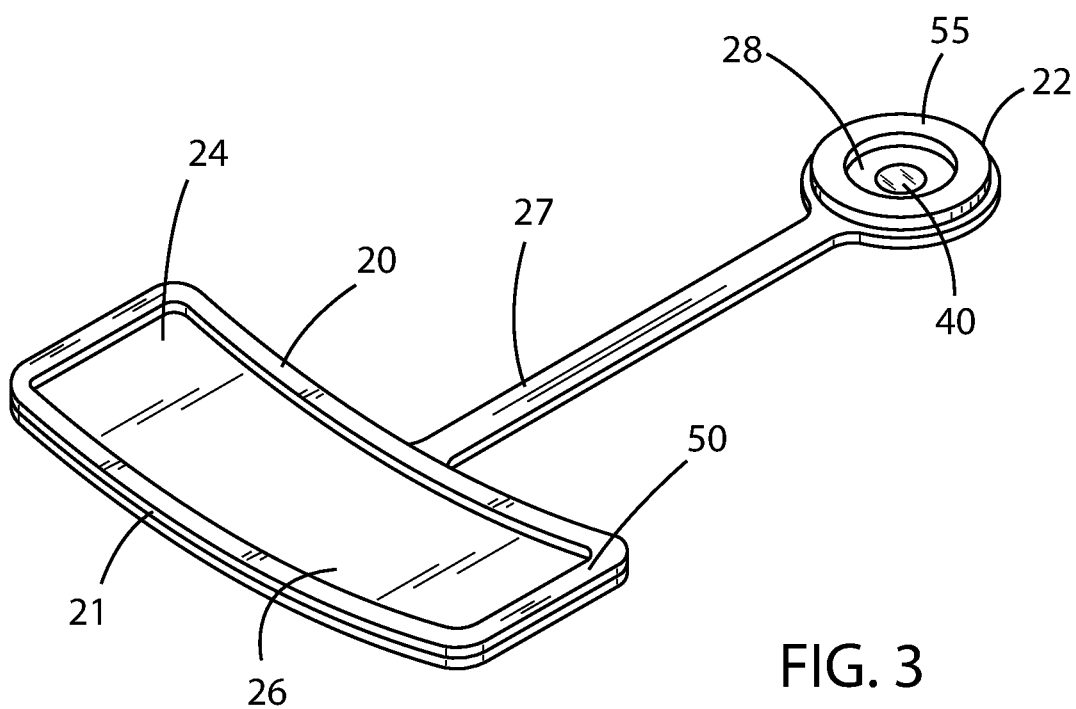
FIG. 3 is a lower perspective view of a physiological sensor system in accordance with an example embodiment.

FIGS. 1-3 illustrate an exemplary housing 20 utilized for removably securing a sensor 40 to a garment 60. It should be appreciated that the shape, configuration, size, and orientation of the housing 20 may vary in different embodiments. What is shown and described herein is merely an exemplary embodiment of the housing 20 and should not be construed as limiting with respect to shape, size, configuration, or orientation.

As shown in FIG. 1, the housing 20 may comprise a first end 21 and a second end 22. In the embodiment shown in the figures, the housing 20 includes a base 26 at its first end 21 and a rounded tip 28 at its second end 22; with a linkage 27 connected between the base 26 and the tip 28. It should be appreciated that other configurations may be utilized. In some embodiments, the base 26 and/or linkage 27 may be omitted.

As shown in FIGS. 2-3, the housing 20 may include an outer surface 23 and an inner surface 24. The outer surface 23 of the housing 20 may include an indicator 38 such as a light, speaker, or display through which information of any condition detected by the sensor 40 may be provided to the user. Although not shown, the outer surface 23 of the housing 20 could include various controls, such as buttons or a touch screen which may be utilized to control operation of the physiological sensor system 10 or to provide various information to the user.

The inner surface 24 of the housing 20 may include the sensor 40, such as a reflectance probe adapted to emit light outwardly (and capture reflected light) from the inner surface 24 of the housing 20. The inner surface 24 of the housing 20 may also include one or more connectors 50, 55 or fasteners 53, 59 adapted to removably connect the housing 20 to the garment 60. In some embodiments, the connectors 50, 55 may comprise magnetic rings adapted to ensure proper alignment of the sensor 40 when the housing 20 is connected to the garment 60.

Figure 4:
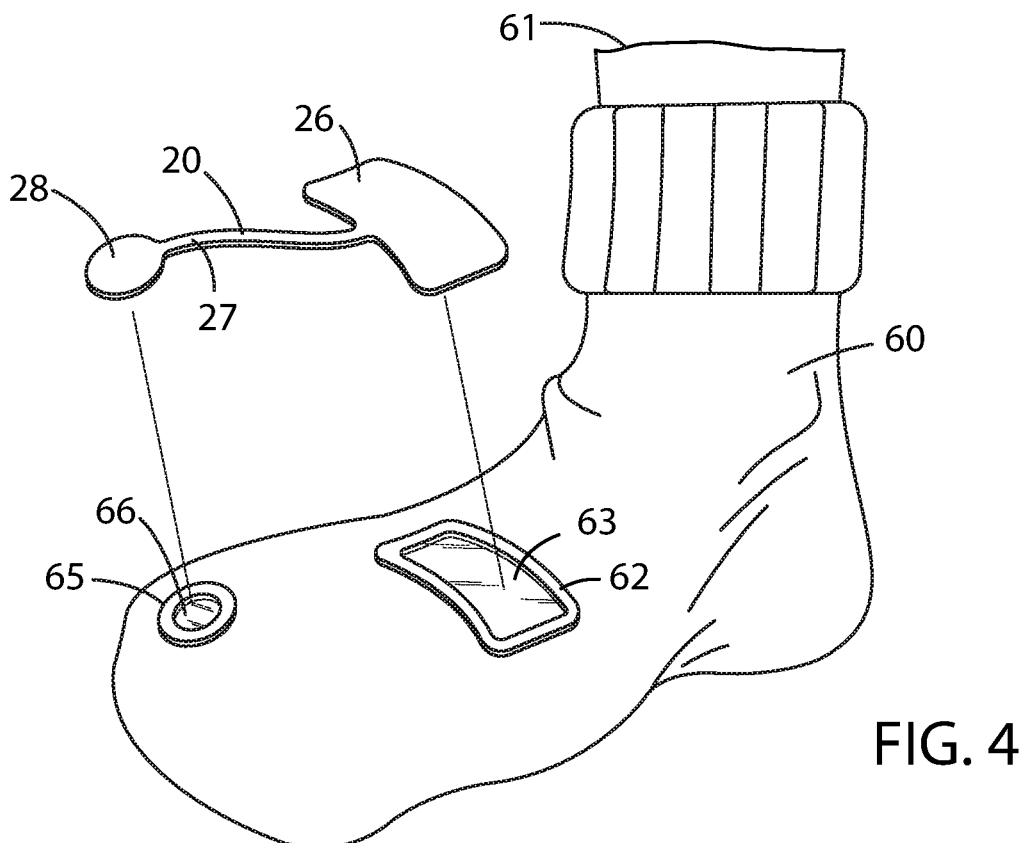
FIG. 4 is an upper perspective view of a physiological sensor system aligned for connection to a sock in accordance with an example embodiment.
Figure 7:
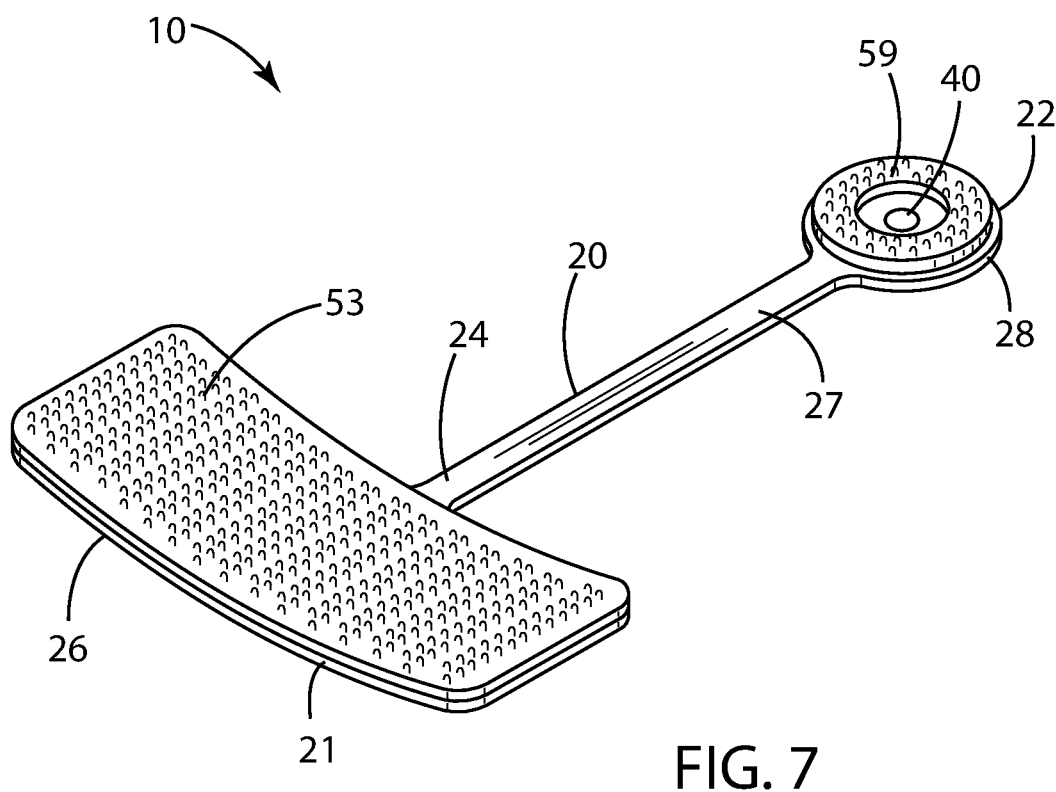
FIG. 7 is an upper perspective view of a physiological sensor system which utilizes hook-and-loop fasteners in accordance with an example embodiment.
Figure 8:
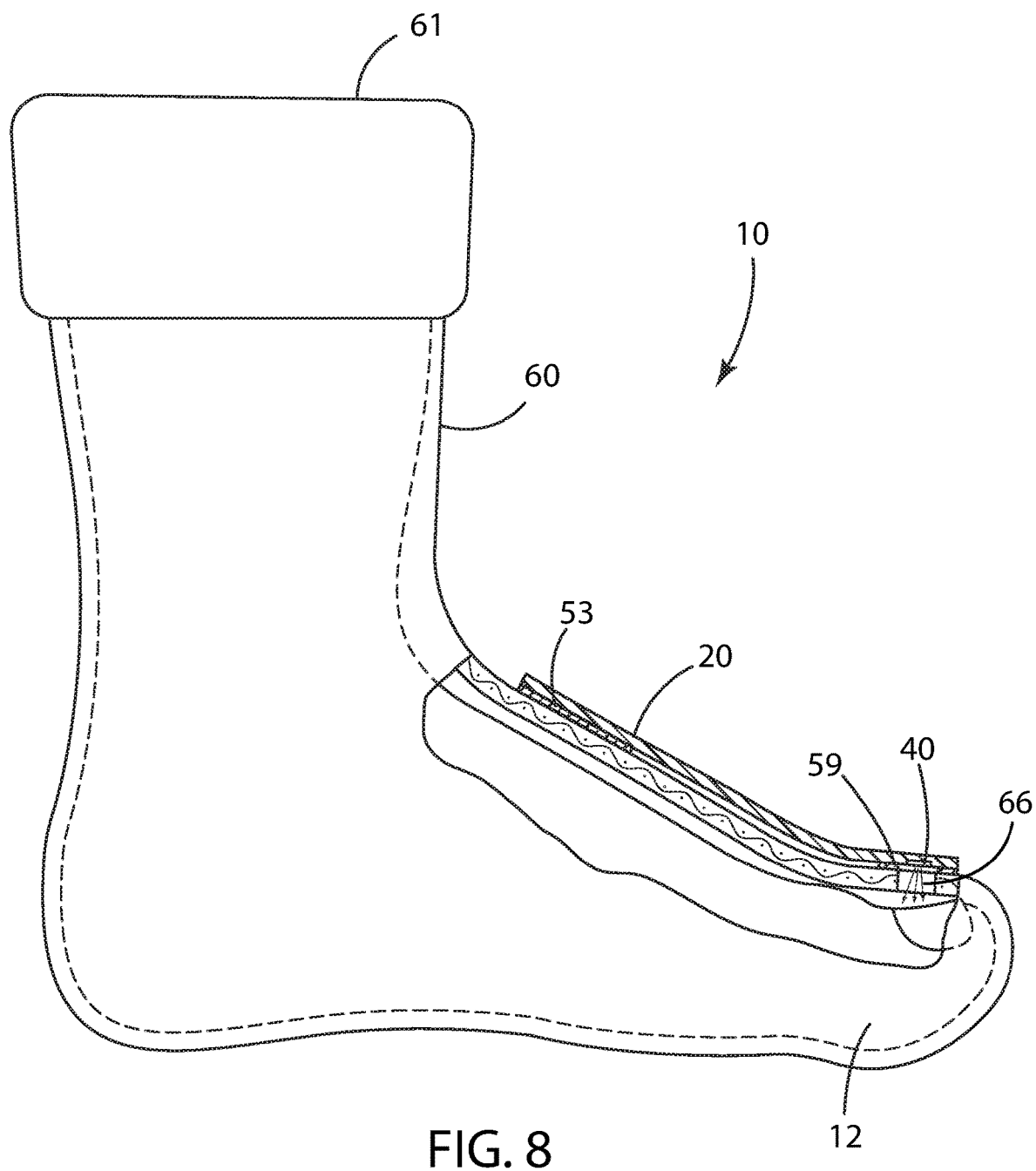
FIG. 8 is a side sectional view of a physiological sensor system in use with a sock in accordance with an example embodiment.

In the exemplary embodiment shown in FIG. 4, the housing 20 is illustrated as comprising a rectangular base 26 adapted to be removably connected to the garment 60. The base 26 may include a base connector 50 on its inner surface 24 such as shown in FIG. 3. The base connector 50 may comprise a rectangular-shaped magnet as shown in FIG. 3. Alternatively, the base 26 may include a base fastener 53 on its inner surface 24 such as shown in FIG. 7. Various other methods may be utilized for removably connecting the base 26 to the garment 60. In some embodiments, the base 26 may be sewn into the garment 60 or clipped to the garment 60.

The base 26 may house the control unit 30 of the present invention, such as a power source 32, controller 34, and/or transceiver 36. Any indicators 38 may also be positioned on the base 26 of the housing 20. While not shown in the figures, some embodiments may include a sensor 40 in the base 26 of the housing 20. For example, a sensor 40 comprised of an accelerometer adapted to detect positional data may be positioned in the base 26 of the housing 20. This type of sensor 40 may be useful for determining body position of a wearer of the garment 60.

As shown in FIG. 1, the housing 20 may also include a linkage 27 extending from the base 26. The linkage 27 may comprise a rigid or flexible, elongated member which connects between the base 26 and the tip 28 of the housing 20. The linkage 27 may be manipulated to position the tip 28 of the housing 20 with the sensor 40 with respect to the base 26 of the housing 20.

A conduit 29 may extend through the linkage 27 to connect the control unit 30 to the sensor 40 in wired embodiments. In other embodiments, such a conduit 29 may be unnecessary if the control unit 30 and sensor 40 are wirelessly interconnected. Although the figures illustrate that the linkage 27 is not directly connected to the garment 60, it should be appreciated that in some embodiments the linkage 27 could be directly connected to the garment 60 such as via a hook-and-loop fastener or an additional magnet.

As shown in FIG. 1, the housing 20 may include a tip 28 at the distal end of the linkage 27. The tip 28 may house the sensor 40. For example, if the sensor 40 is a pulse oximeter, the inner surface 24 of the tip 28 of the housing 20 may house the reflectance probe which will emit light from the inner surface 24 of the tip 28 of the housing 20. The sensor 40 may be connected to the outside of the tip 28 of the housing 20 in some embodiments.

As shown in FIG. 1, the tip 28 may comprise a rounded configuration. The inner surface 24 of the tip 28 of the housing 20 may include a tip connector 55 or tip fastener 59 for removably connecting the tip 28 of the housing 20 to the garment 60. In the embodiment of FIG. 3, the tip 28 of the housing 20 includes a tip connector 55 comprised of a ring magnet which surrounds the sensor 40. In the embodiment of FIG. 7, the tip 28 of the housing 20 includes a tip fastener 59 comprised of hook-and-loop fastener material such as Velcro. Various other methods may be utilized for removably connecting the tip 28 of the housing 20 to the garment 60.

Figure 13:
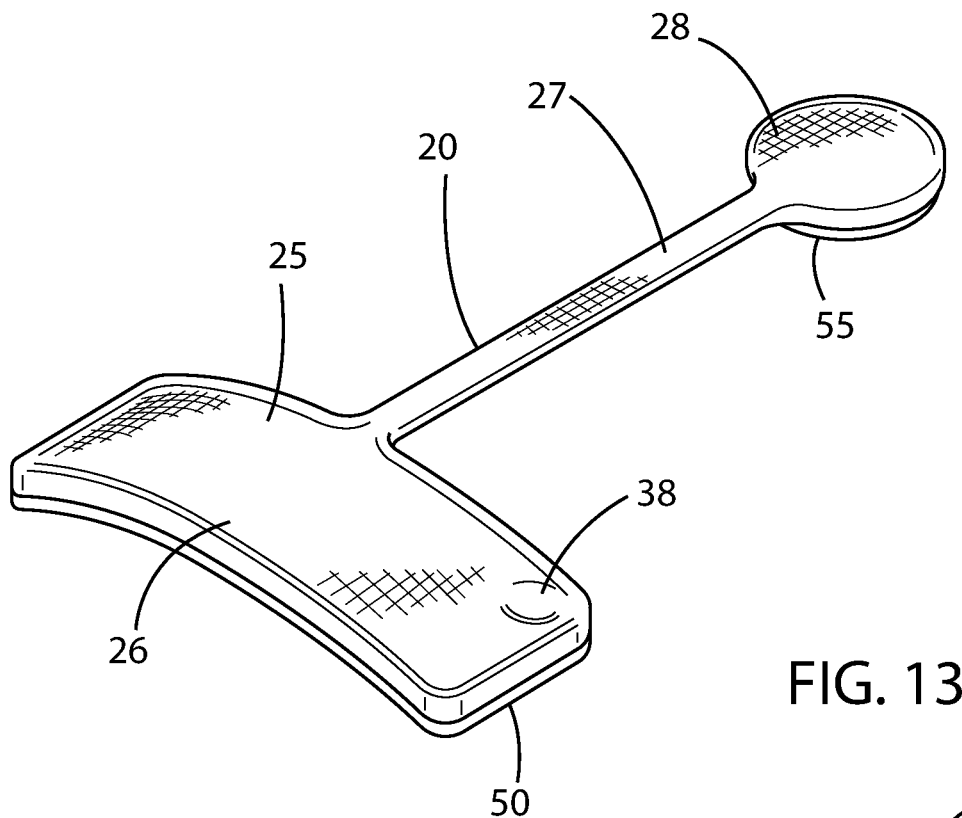
FIG. 13 is an upper perspective view of a physiological sensor system utilizing a sleeve in accordance with an example embodiment.
Figure 14:
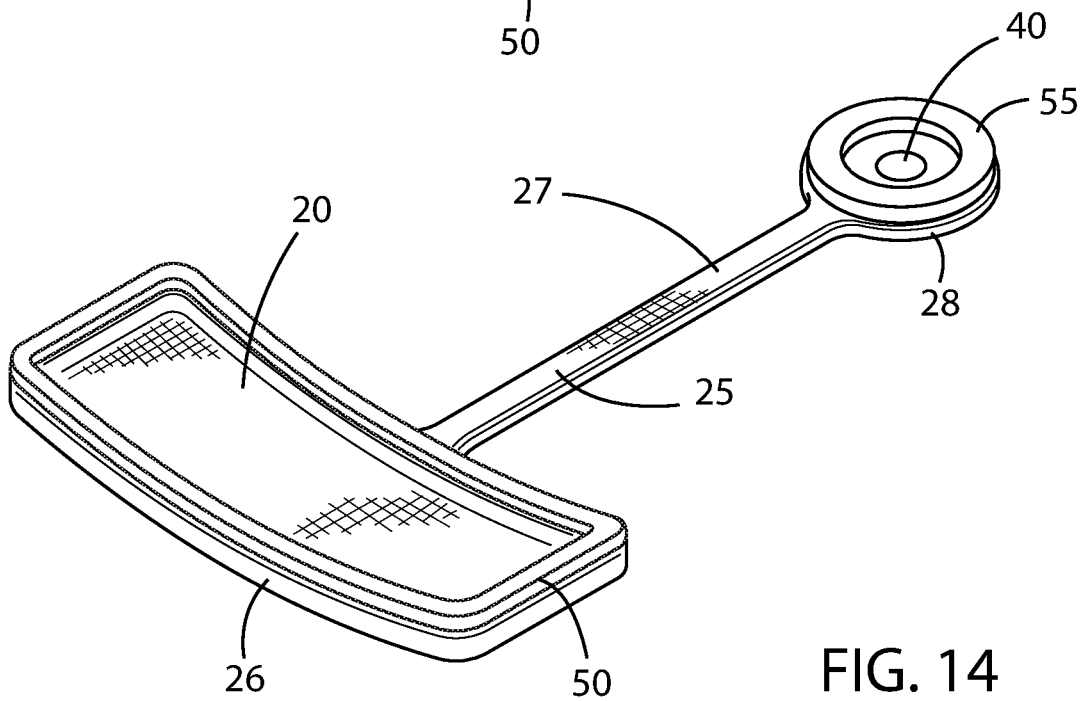
FIG. 14 is a lower perspective view of a physiological sensor system utilizing a sleeve in accordance with an example embodiment.
Figure 15:
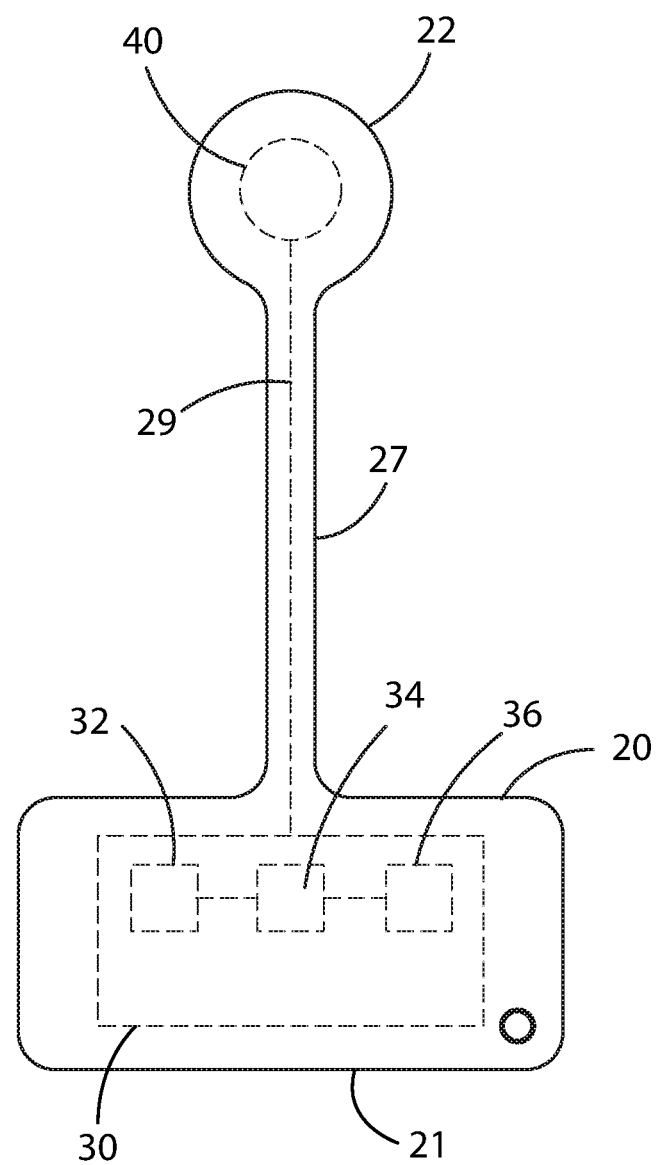
FIG. 15 is an upper view and block diagram of a physiological sensor system in accordance with an example embodiment.

In some embodiments, a sleeve 25 may be provided to cover the housing 20 and/or sensor 40. The sleeve 25 may be sewn shown or may have a flap or slit through which the housing 20 and/or sensor 40 may be easily removed from or inserted into the sleeve 25. The sleeve 25 may comprise a fabric material which will not irritate the skin. FIGS. 13-14 illustrate an embodiment in which a sleeve 25 is utilized; with the connectors 50, 55 being on the exterior of the sleeve 25.

C. Control Unit and Sensor.

Figure 11:
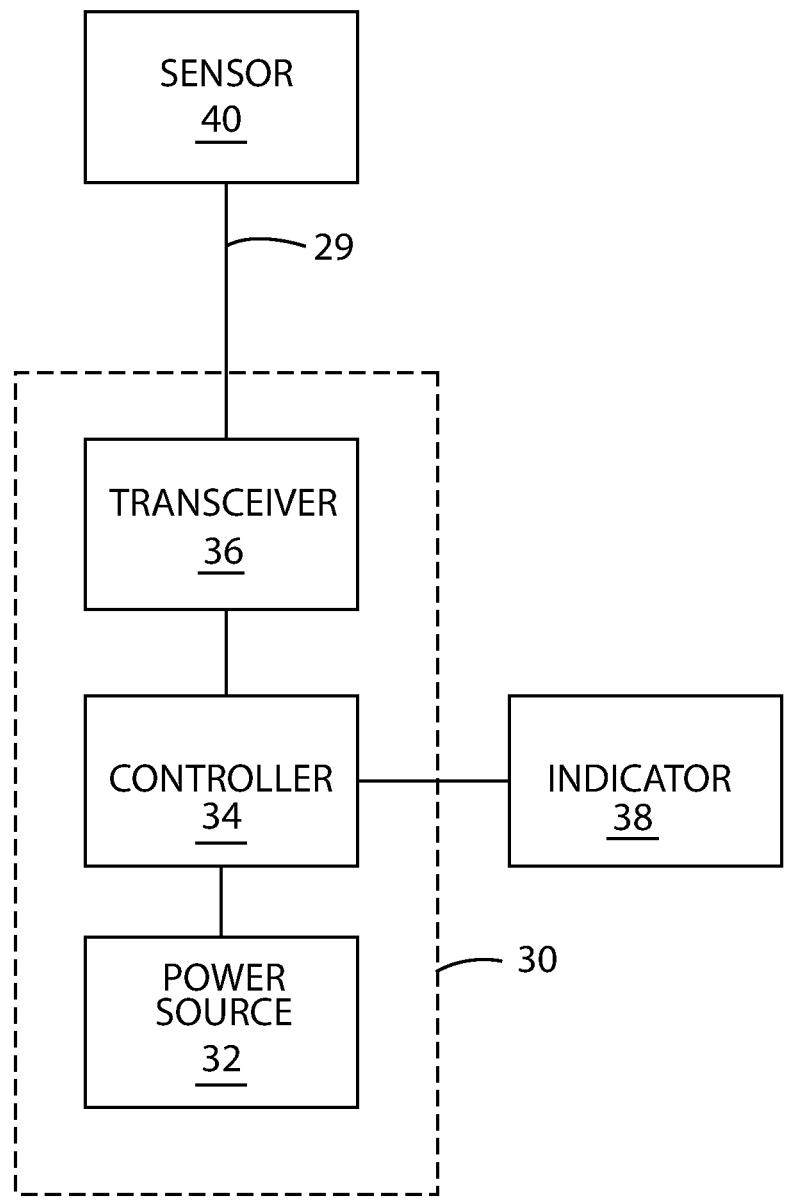
FIG. 11 is a block diagram of a first exemplary embodiment of a physiological sensor system.
Figure 12:
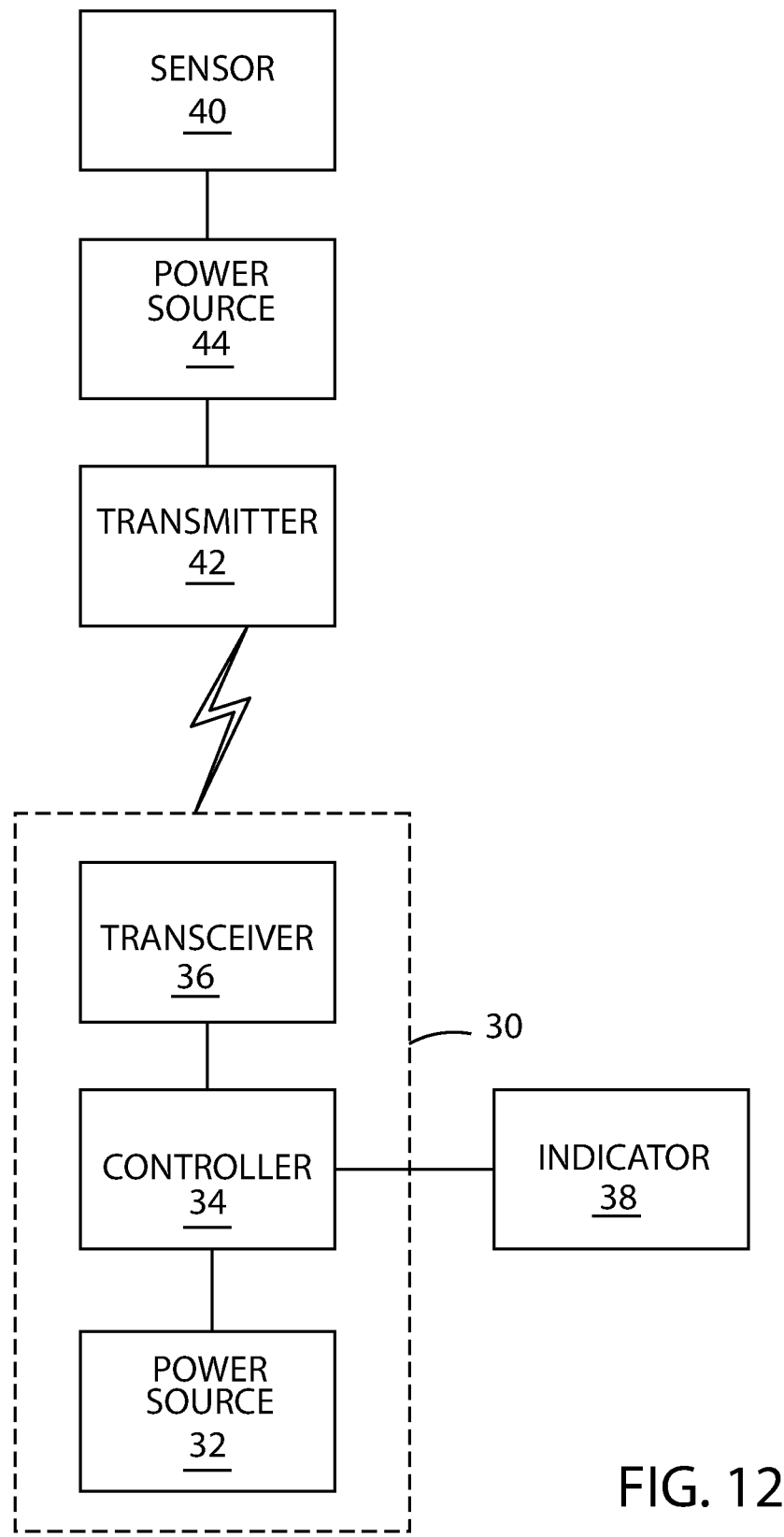
FIG. 12 is a block diagram of a second exemplary embodiment of a physiological sensor system.

As best shown in FIGS. 11-12, the physiological sensor system 10 may include a control unit 30 and a sensor 40; with the control unit 30 being adapted to receive and process data from the sensor 40. The control unit 30 is illustrated as being positioned in the base 26 of the housing 20 in FIG. 14. However, it should be appreciated that the control unit 30 could be integrated with the sensor 40 in some embodiments. In other embodiments, the control unit 30 may be wirelessly connected to the sensor 40. For example, the control unit 30 could be a separate device that could be clipped to a belt or the like.

FIGS. 11-12 illustrate an exemplary embodiment of a control unit 30 for use with the physiological sensor system 10. FIG. 11 illustrates a wired connection between the control unit 30 and the sensor 40. FIG. 12 illustrates a wireless connection between the control unit 30 and the sensor 40.

The control unit 30 is illustrated as comprising a power source 32, a controller 34, and a transceiver 36. The power source 32 may be any type of source of power, such as a battery or the like. The controller 34 may comprise analog circuitry or digital electronics such as a microcontroller. The transceiver 36 may be utilized to communicate with the sensor 40 and/or an indicator 38.

The indicator 38 is controlled by the control unit 30. The indicator 38 may comprise a light, a speaker, a display, or the like. The indicator 38 may perform various functions, such as but not limited to indicating whether the device is powered on or indicating various conditions (such as low oxygen levels). In some embodiments, the control unit 30 may communicatively interconnect with an indicator 38 comprised of a mobile device or computer.

In the exemplary embodiment shown in FIG. 12, the sensor 40 may include its own power source 44 and transmitter 42. Although not shown, the sensor 40 could have its own separate control unit such as a microcontroller or control circuitry. It should be appreciated that, in some embodiments, the sensor 40 may share a power source 32 with the control unit 30. The transmitter 42 on the sensor 40 may be utilized to transmit data related to conditions detected by the sensor 40 to the control unit 30 or an indicator 38.

Various types of sensors 40 may be utilized. A pulse oximeter including a reflectance probe may be utilized to sense pulse rate and oxygenation levels. Transmittance type sensors 40 may also be utilized (such sensors 40 would wrap around the big toe or finger). An accelerator may be utilized to detect positional data. While optical sensors 40 are primarily discussed, it should be appreciated that other types of physiological sensors may be utilized, such as contact sensors that require contact with the skin. In such an embodiment, the garment windows 63, 66 may be comprised of openings that allow the sensor 40 to the contact the skin.

D. Connectors.

The manner in which the sensor 40 is connected to the garment 60 may vary in different embodiments. FIGS. 1-5 illustrate an embodiment which utilizes magnetic connectors 50, 55, 62, 65. In such an embodiment, the base 26 of the housing 20 includes a base connector 50 having an outer edge 51 encapsulating a central opening 52. Similarly, the tip 28 of the housing 20 may include a tip connector 55 having an outer edge 51 encapsulating a central opening 52.

In such an embodiment, corresponding garment connectors 62, 65 are positioned on the garment 60 so as to removably engage with the corresponding connectors 50, 55 on the housing 20. As shown in FIG. 4, the garment 60 may include a first garment connector 62 surrounding a first window 63. The base connector 50 is adapted to removably engage with the first garment connector 62 such that the base 26 is positioned over the first window 63.

Figure 6:
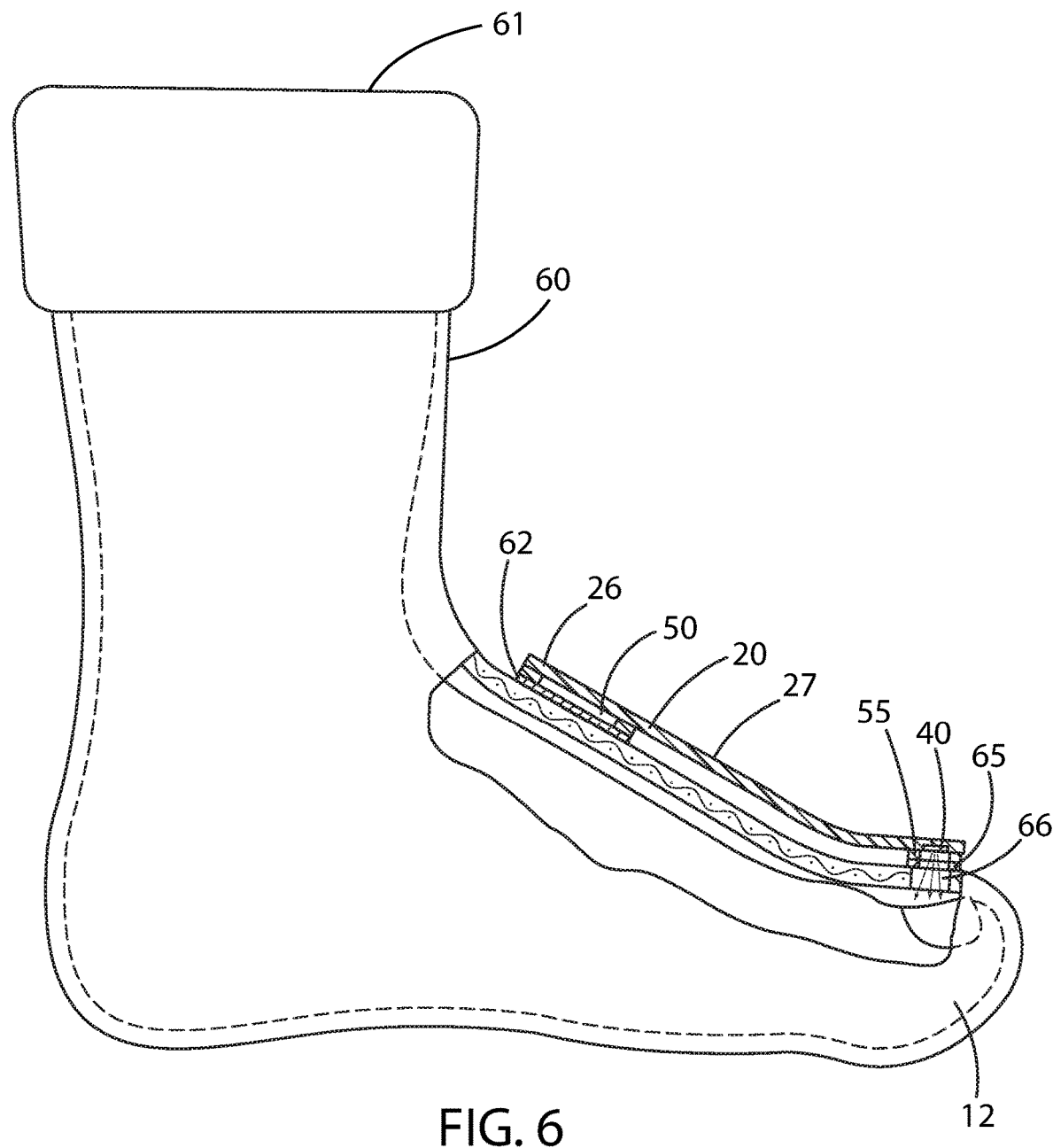
FIG. 6 is a side sectional view of a physiological sensor system in use with a sock in accordance with an example embodiment.

As shown in FIG. 4, the garment 60 may include a second garment connector 65 surrounding a second window 66. The tip connector 55 is adapted to removably engage with the second garment connector 65 such that the sensor 40 in the tip 28 is positioned over the second window 66. In this manner, an optical sensor may direct a beam of light through the second window 66 to the underlying body 12 such as shown in FIG. 6.

In the embodiment shown in FIG. 3, the base connector 50 comprises a rectangular-shaped magnetic loop. The first garment connector 62 comprises a rectangular-shaped magnetic loop of the same shape and size of the base connector 50. In this manner, the base connector 50 and first garment connector 62 may automatically align into magnetic engagement when brought close to each other.

Similarly, FIG. 3 illustrates that the tip connector 55 comprises a ring-shaped magnetic loop. The second garment connector 65 comprises a ring-shaped magnetic loop of the same shape and size of the tip connector 55. In this manner, the tip connector 55 and second garment connector 65 may automatically align into magnetic engagement when brought close to each other such that the sensor 40 may direct a light beam through the central opening 57 of the tip connector 55 and the second window 66 of the second garment connector 65 to illuminate the body 12.

The use of similarly-shaped and sized magnets allows for easy and automatic alignment of the housing connectors 50, 55 with the garment connectors 62, 66. This ensures a proper reading and will also maintain the connection even when a wearer is on the move or during long periods of restless sleep.

FIG. 7 illustrates an alternate embodiment in which hook-and-loop fasteners are utilized to removably connect the housing 20 to the garment 60. FIG. 7 illustrates that the base 26 of the housing 20 may include a base fastener 53 comprised of a hook-and-loop material. This base fastener 53 may be adapted to connect directly to the garment 60 or may interconnect with corresponding fastener material on the garment 60 itself.

FIG. 7 illustrates that the tip 28 of the housing 20 may include a tip fastener 59 comprised of a hook-and-loop material. As shown in FIG. 7, the tip fastener 59 is ring-shaped so as to allow light from the sensor 40 to emanate onto the body 12. The tip fastener 59 may be adapted to connect directly to the garment 60 or may interconnect with corresponding fastener material on the garment 60 itself.

Figure 5:
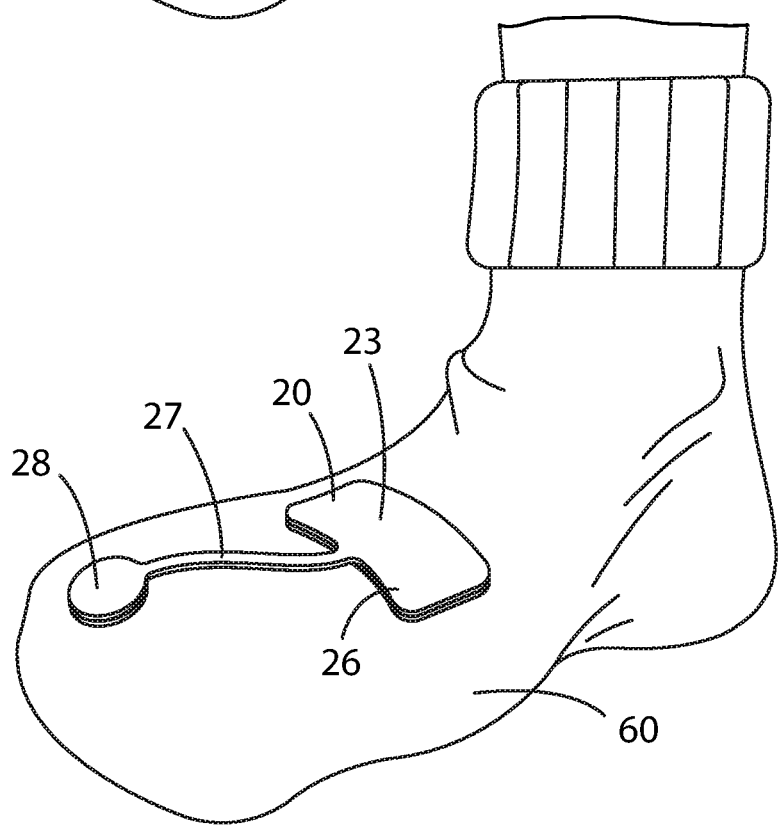
FIG. 5 is an upper perspective view of a physiological sensor system connected to a sock in accordance with an example embodiment.
Figure 9:
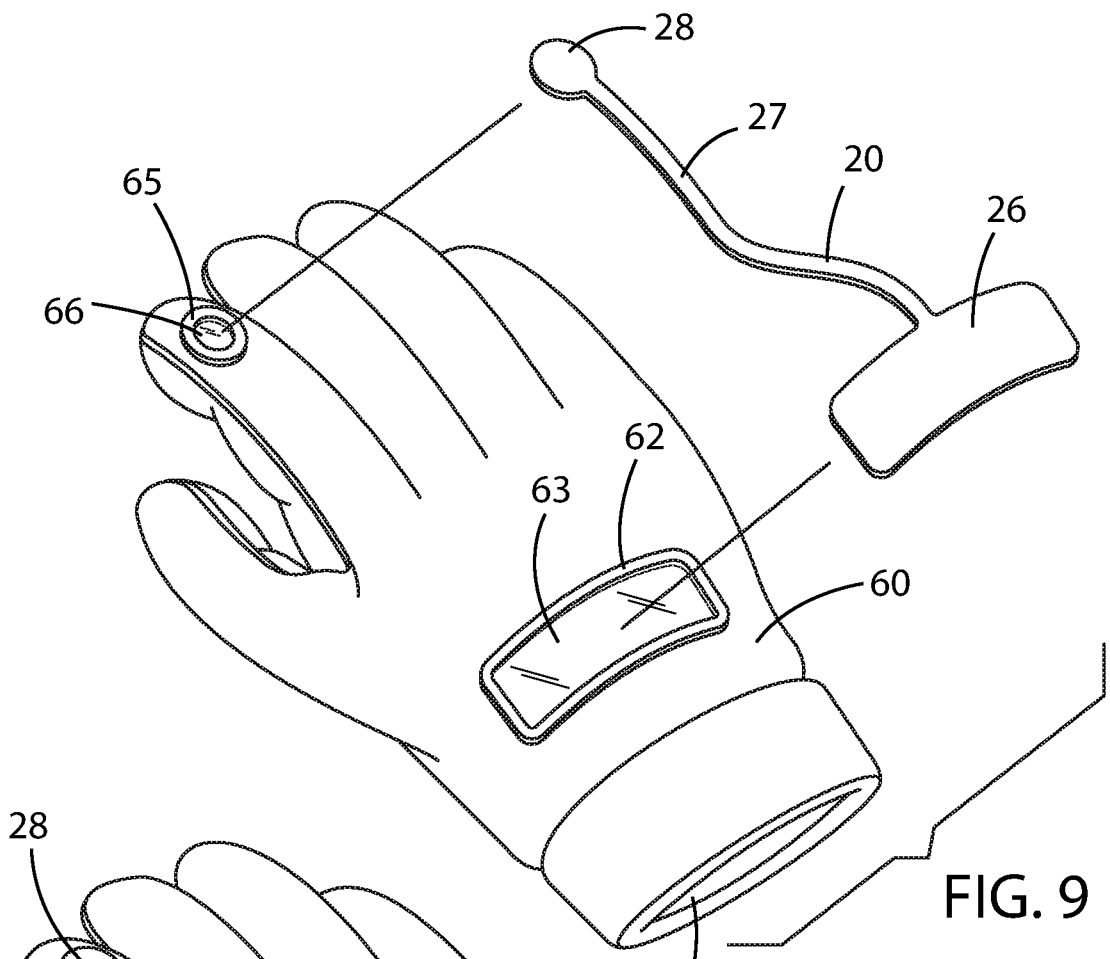
FIG. 9 is an upper perspective view of a physiological sensor system aligned for connection to a glove in accordance with an example embodiment.
Figure 10:
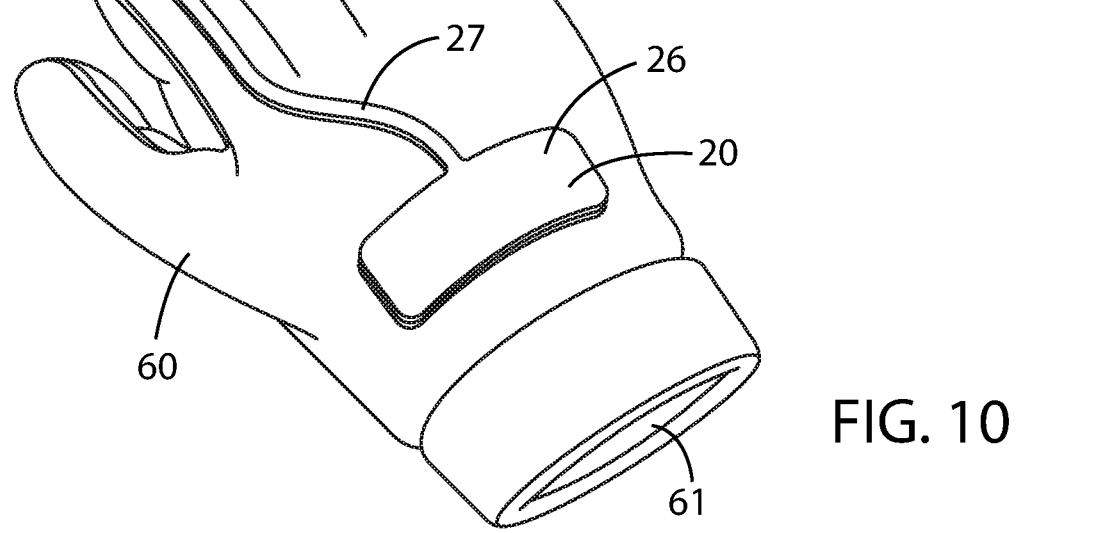
FIG. 10 is a side sectional view of a physiological sensor system in use with a glove in accordance with an example embodiment.

It should be appreciated that a wide range of garments 60 may be utilized. FIGS. 4-6 illustrates a garment 60 comprised of a sock having an opening 61 through which a foot may be positioned in the sock. In such an embodiment, the sensor 40 may be positioned over the big toe. FIGS. 9-10 illustrates a garment 60 comprised of a glove having an opening 61 through which a hand may be positioned in the glove. In such an embodiment, the sensor 40 may be positioned over the index finger. It should be appreciated that other garments may be utilized, such as hats, headbands, or the like.

Figure 16:
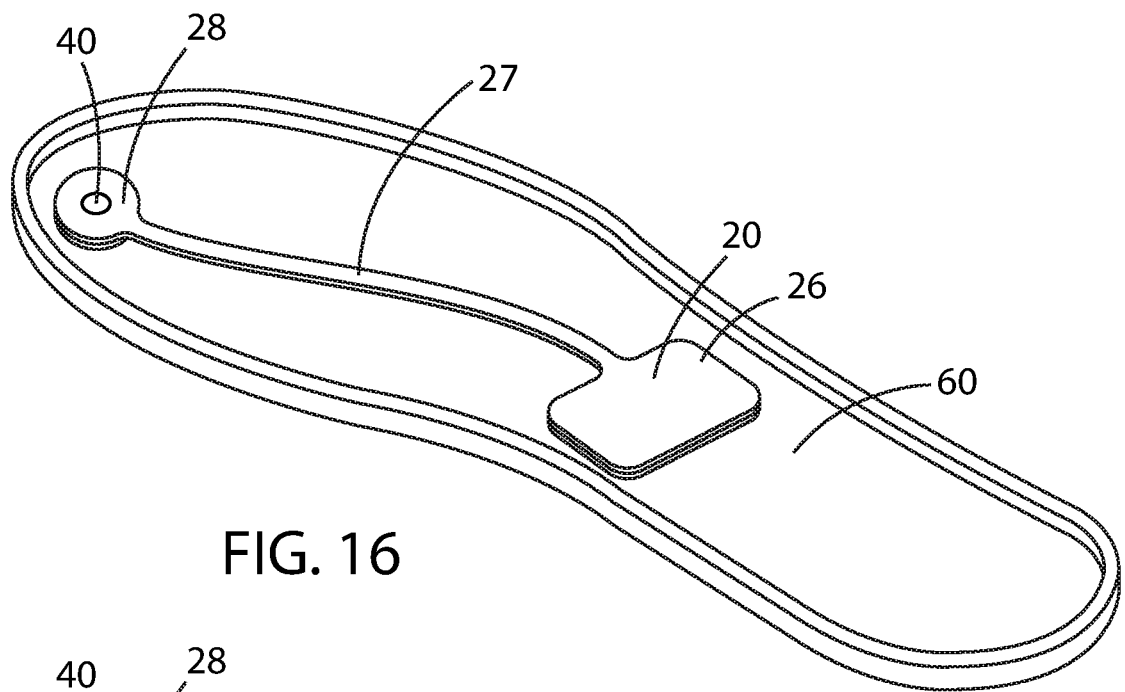
FIG. 16 is a top view of a physiological sensor system aligned to be installed on a shoe insole in accordance with an example embodiment.
Figure 17:
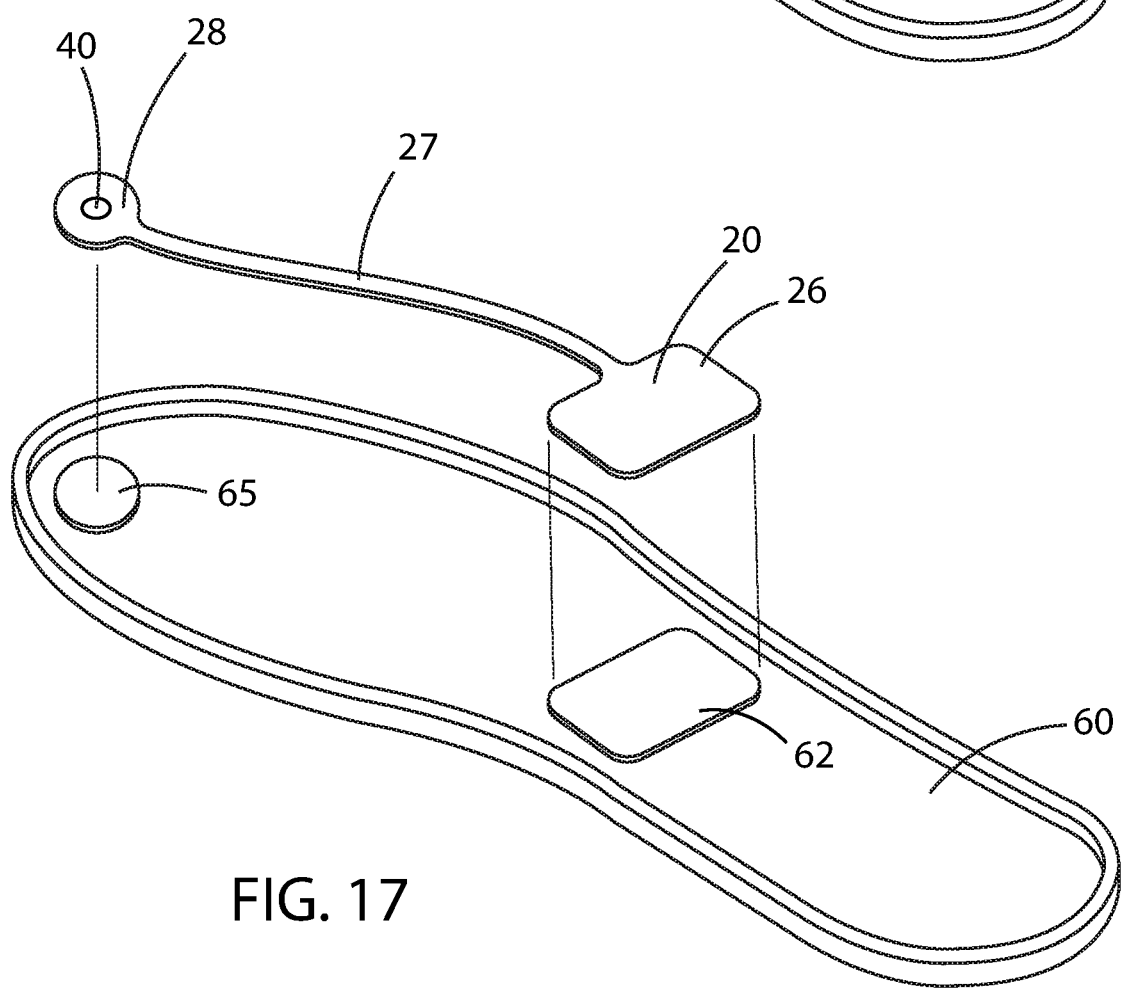
FIG. 17 is a top view of a physiological sensor system installed on a shoe insole in accordance with an example embodiment.

FIGS. 16-17 illustrates a garment 60 comprised of a shoe insole. In such an embodiment, the sensor 40 may be positioned underneath the big toe. As shown in FIG. 17, the shoe insole may include a first garment connector 62 under the base of the foot and a second garment connector 65 under the position where the big toe would be. Windows 63, 65 may be unnecessary in such an embodiment if the sensor 40 points upwardly from the top of the housing 20 as shown in FIG. 17. If the sensor 40 is positioned on the bottom of the housing 20, windows 63, 65 may be utilized to direct the beam of light upwardly to the big toe.

E. Operation of Preferred Embodiment.

In use, the housing 20 is first connected to the garment 60 using either the connectors 50, 55, 62, 65 or the fasteners 53, 59. In FIG. 4, a housing 20 is aligned for connection to a garment 60 comprised of a sock. As shown in that embodiment, the sock includes a first garment connector 62 above the navicular region and a second garment connector 65 over the big toe.

The base connector 50 is first aligned with and magnetically connected to the first garment connector 62. The magnetic attraction will automatically align and connect the base 26 of the housing 20 to the garment 60 over the navicular region of the foot. The tip connector 55 may then be aligned with and magnetically connected to the second garment connector 65. The magnetic attraction will automatically align and connect the tip 28 of the housing 20 to the garment 60 over the big toe so that the sensor 40 may direct a light beam onto the big toe such as shown in FIG. 6.

FIG. 9 illustrates a housing aligned for connection to a garment 60 comprised of a glove. As shown in that embodiment, the glove includes a first garment connector 62 above the back of the hand and a second garment connector 65 over the index fingernail.

The base connector 50 is first aligned with and magnetically connected to the first garment connector 62. The magnetic attraction will automatically align and connect the base 26 of the housing 20 to the garment 60 over the back of the hand. The tip connector 55 may then be aligned with and magnetically connected to the second garment connector 65. The magnetic attraction will automatically align and connect the tip 28 of the housing 20 to the garment 60 over the nail of the index finger so that the sensor 40 may direct a light beam onto the index finger.

In embodiments such as shown in FIG. 7 which utilize fasteners 53, 59, the housing 20 may similarly be removably connected to the garment 60. The base fastener 53 may first be secured to the garment 60 at a desired location. In some embodiments, the base fastener 53 may engage directly with the garment 60 itself. In other embodiments, the garment 60 may have its own strips of hook-and-loop material adapted to engage with the base fastener 53.

With the base fastener 53 so secured, the tip fastener 59 may be engaged around the window 66 on the garment 60 which is above the portion of the body 12 to be detected. The tip fastener 59 may engage directly with the garment 60 itself, or the garment may include its own ring of hook-and-loop material surrounding the window 66 to which the tip fastener 59 may removably engage. In either case, the tip fastener 59 should be connected such that a light beam emanating from the sensor 40 may pass to the body 12 without undue interference.

Once the sensor 40 is connected to the garment 60, the physiological sensor system 10 is ready for use. The sensor 40 may automatically activate. In an exemplary embodiment where tip connector 55 comprises a ring magnet, the control unit 30 may be communicatively interconnected with the tip connector 55 so as to detect when the tip connector 55 has magnetically engaged with the corresponding garment connector 65. In such an exemplary embodiment, the sensor 40 may be activated upon detection of such a connection between the sensor 40 and the garment 60. In other embodiments, manual activation may be required. Timers may also be provided to set a duration of time for the sensor 40 to operate.

When activated, the sensor 40 will detect various conditions and transmit data to the control unit 30 for processing. For example, if the sensor 40 comprises a transmittance-type or reflectance-type oximeter, the sensor 40 may continuously detect pulse rate, oxygenation levels, or other physiological conditions. If the sensor 40 comprises an accelerometer, the sensor 40 may continuously detect positional data such as a body position of a wearer.

The control unit 30 may receive and process data from the sensor 40. The control unit 30 may be programmable to perform various functions. For example, the control unit 30 may be configured to set off an indicator 38 if certain conditions have been reached. By way of example, the control unit 30 could be configured to set off an indicator 38 such as an audible alarm or visible light when oxygenation levels dip below a threshold or when the body is detected to be in an undesirable position. In some embodiments, the control unit 30 may communicate with an indicator 38 such as a mobile device (tablet, computer, phone, etc.) that may display separately the collected data.

Unless otherwise defined, all technical and scientific terms used herein have the same meaning as commonly understood by one of ordinary skill in the art to which this invention belongs. Although methods and materials similar to or equivalent to those described herein can be used in the practice or testing of the physiological sensor system, suitable methods and materials are described above. All publications, patent applications, patents, and other references mentioned herein are incorporated by reference in their entirety to the extent allowed by applicable law and regulations. The physiological sensor system may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A sensor system, comprising: a garment adapted to contact a portion of a body;
   a window formed in the garment, wherein the portion of the body is visible through the window;
   a sensor connected to the garment for detecting a physiological condition, wherein the sensor is removably connected to the garment above the window such that the sensor is on a side of the garment not in contact with the body when the garment is worn;
   a control unit for processing data from the sensor, wherein the control unit is communicatively interconnected with the sensor; and
   an indicator communicatively interconnected with the control unit, the indicator being adapted to provide an indication of the physiological condition detected by the sensory wherein the sensor includes a reflectance probe, wherein the reflectance probe is adapted to direct light through the window and on to the portion of the body.

2. The sensor system of claim 1, wherein the garment comprises a garment connector adapted to engage with the sensor so as to removably connect the sensor to the garment.

3. The sensor system of claim 2, wherein the garment connector comprises a first ring magnet which surrounds the window.

4. The sensor system of claim 3, wherein the sensor comprises a second ring magnet adapted to removably engage with the first ring magnet to removably connect the sensor to the garment.

5. The sensor system of claim 1, wherein the sensor comprises a hook-and-loop fastener adapted to removably engage with the garment.

6. The sensor system of claim 1, wherein the control unit is removably connected to the garment.

7. The sensor system of claim 6, further comprising a conduit connected between the control unit and the sensor.

8. The sensor system of claim 6, wherein the control unit comprises a power source and a microcontroller.

9. The sensor system of claim 8, wherein the control unit comprises a transceiver, wherein the transceiver is communicatively interconnected with the sensor.

10. The sensor system of claim 1, wherein the indicator comprises a light.

11. The sensor system of claim 1, further comprising a sleeve secured around the sensor, wherein the sleeve is removably connected to the garment.

12. The sensor system of claim 1, wherein the window comprises an opening.

13. The sensor system of claim 1, wherein the window comprises a semi-transparent material.

14. The sensor system of claim 1, wherein the sensor is comprised of an optical sensor.

15. The sensor system of claim 1, wherein the sensor is comprised of a pulse oximeter reflectance probe adapted to detect an oxygen saturation level and a pulse rate.

16. The sensor system of claim 15, wherein the sensor is further comprised of an accelerometer adapted to detect positional data of the body.

17. The sensor system of claim 1, wherein the indicator comprises a mobile device.

18. A sensor system, comprising:
    a garment adapted to contact a portion of a body;
    a window formed in the garment, wherein the portion of the body is visible through the window;
    a housing including a base, a linkage, and a tip, wherein the linkage is connected between the base and the tip;
    a physiological sensor positioned at the tip of the housing, wherein the physiological sensor is comprised of an optical reflectance probe adapted to detect an oxygen saturation level and a pulse rate;
    a control unit for processing data from the physiological sensor, wherein the control unit is communicatively interconnected with the physiological sensor;
    a first ring magnet on the garment, wherein the first ring magnet surrounds the window formed in the garment;
    a second ring magnet on the tip of the housing, wherein the second ring magnet is adapted to align with and removably engage with the first ring magnet so as to removably connect the sensor to the garment, wherein the housing is removably connected to the garment such that the physiological sensor is positioned above the window such that the sensor is on a side of the garment not in contact with the body when the garment is worn; and
    an indicator communicatively interconnected with the control unit, the indicator being adapted to provide an indication of a physiological condition detected by the physiological sensor, wherein the indicator is further adapted to provide an indication of an operating condition of the physiological sensor.

* * * * *